United States Patent [19]

Graham

[11] 4,031,142

[45] June 21, 1977

[54] PROCESS FOR THE DIRECTED CHLORINATION OF ALKYLBENZENES

[75] Inventor: John C. Graham, Warren, Mich.

[73] Assignee: Hooker Chemicals & Plastics Corporation, Niagara Falls, N.Y.

[22] Filed: Aug. 1, 1975

[21] Appl. No.: 601,690

[52] U.S. Cl. .................... 260/650 R; 252/429 R; 252/429 A
[51] Int. Cl.² ........................................ C07C 25/04
[58] Field of Search ........................... 260/650 R

[56] References Cited

UNITED STATES PATENTS

| | | | |
|---|---|---|---|
| 1,741,305 | 12/1929 | Jaeger | 260/650 R |
| 1,946,040 | 2/1934 | Stoesser et al. | 260/650 R |
| 3,226,447 | 12/1965 | Bing et al. | 260/650 R |

*Primary Examiner*—D. Horwitz
*Attorney, Agent, or Firm*—Peter F. Casella; William J. Crossetta, Jr.; Arthur S. Cookfair

[57] ABSTRACT

A process for the production of nuclear chlorinated alkylbenzenes comprises reacting an alkylbenzene with chlorine in the presence of a catalyst system comprising a Lewis acid catalyst and a thianthrene co-catalyst. The nuclear chlorinated alkylbenzene products prepared in this manner are characterized by a substantially reduced ratio of orthochloro to parachloro isomer.

12 Claims, No Drawings

PROCESS FOR THE DIRECTED CHLORINATION OF ALKYLBENZENES

BACKGROUND OF THE INVENTION

The chemical reaction of chlorine with alkylbenzenes, such as toluene, to prepare nuclear substituted chloro-compounds such as monochlorotoluene, is well known and of considerable commercial importance. Such reactions are generally carried out in the presence of a chlorination catalyst such as antimony chloride, ferric chloride, aluminum chloride, and the like. The usual products of such reactions are a mixture of various mono-chlorinated and/or polychlorinated compounds and various positional isomers of these. For example, in the liquid phase substitution-chlorination of toluene by reaction of chlorine and toluene, to form monochlorotoluene, the usual product is a mixture of orthochlorotoluene and parachlorotoluene which may, in addition, contain varying amounts of other chlorinated products such as metachlorotoluene, dichlorotoluene, polychlorotoluenes and benzylic chlorides. Of the major reaction products, that is orthochlorotoluene and parachlorotoluene, the latter is the most commercially valuable. In the past, considerable effort has been expended in attempts to direct the chlorination reaction in such a manner as to lower the ratio of orthochlorotoluene to parachlorotoluene, that is, to discover reaction conditions under which the formation of parachlorotoluene is favored. Thus, for example, it is known from U.S. Pat. No. 1,946,040 that when alkylbenzenes are reacted with chlorine, the yield of parachlorinated product is improved with the aid of a mixed catalyst comprising sulfur and antimony trichloride and, optionally, iron or lead. In British Pat. No. 1,153,746 (1969) it is disclosed that in the chlorination of toluene in the presence of a ring chlorination catalyst, such as ferric chloride, antimony chloride, and the like, the ratio of orthochloro to parachloro isomers produced may be lowered by the presence of an organic sulfur compound such as thiophene, hexadecylmercaptan, dibenzothiophene or the like. Furthermore, in British Pat. No. 1,163,927 (1969) it is disclosed that the proportion of parachlorotoluene produced may be improved when toluene is chlorinated in the presence of elemental sulfur or an inorganic sulfur compound and a ring-chlorination catalyst such as ferric chloride, aluminum chloride, antimony chloride, zinc chloride, iodine, molybdenum chloride, stannous chloride, zirconium tetrachloride or boron trifluoride. In U.S. Pat. No. 3,226,447, issued Dec. 28, 1965 to Bing et al, it is disclosed that in the substitution - chlorination of benzenes and toluene by chlorine, the ratio of ortho isomer to para isomer in the chlorinated product may be lowered when the reaction is carried out in the presence of an iron, aluminum or antimony halide catalyst and a co-catalyst which is an organic sulfur compound wherein the sulfur is divalent. Examples of such co-catalysts include various mercaptans, mercapto-aliphatic carboxylic acids, aliphatic thiocarboxylic acids, alkyl sulfides, alkyl disulfides, thiophenols, aryl sulfides, aryl disulfides and the like containing divalent sulfur. Although improvements in the yield of parachloroalkylbenzenes may be achieved by means of the various prior art processes, it will be appreciated that still further improvements, especially through the use of more effective para-directing catalysts are desirable.

It is an object of this invention to provide a process for the directed nuclear chlorination of alkylbenzenes whereby the formation of parachloroalkylbenzenes is substantially increased. It is a further object to provide new catalysts for the para-directed halogenation of aromatic compounds, especially alkylbenzenes. These and other objects and advantages of this invention will be apparent from the following description of the present invention.

SUMMARY OF THE INVENTION

In accordance with the present invention there is provided a process for the production of nuclear chlorinated alkylbenzenes which comprises reacting, in the liquid phase, an alkylbenzene with chlorine in the presence of a catalyst system comprising a Lewis acid catalyst and a thianthrene co-catalyst.

A wide variety of Lewis acid catalysts may be employed in the process of the present invention. The term "Lewis acid catalyst " as employed herein includes, in addition to Lewis acids, those compounds or elements that will form Lewis acids under the conditions of the chlorination reaction. Preferred catalysts for this purpose are compounds of antimony, lead, iron, molybdenum and aluminum, including for example, the halides, oxyhalides, oxides, sulfides, sulfates, carbonyls and elemental form of these elements and mixtures of such compounds and most preferably the chlorides of aluminum, antimony, and iron. Typical of the catalysts which may be employed in the process of this invention are aluminum chloride, antimony trichloride, antimony pentachloride, antimony trioxide, antimony tetraoxide, antimony pentaoxide, antimony trifluoride, antimony oxychloride, molybdenum hexacarbonyl, lead sulfide, ferric chloride, ferrous chloride, ferrous sulfate, ferric oxide, ferrous sulfide, iron disulfide, iron pentacarbonyl, iron metal, and the like.

The thianthrene co-catalysts suitable for use in the process of this invention are characterized by the formula

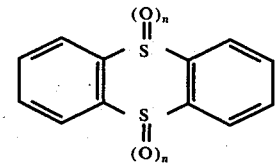

where each $n$ is 0 or 1, and include for example, thianthrene as well as the corresponding mono- and di- sulfoxide compounds as well as mixtures thereof. The preferred co-catalyst is thianthrene.

The amount of catalyst and co-catalyst employed may vary considerably. Thus, substantial benefits in terms of the lowering of the ratio of ortho-to para-isomer in the product may be achieved when the catalyst and co-catalyst are present in a total amount of from less than 0.01 to 5 percent by weight or more, based on the weight of alkylbenzene, and preferably in a molar ratio of catalyst:co-catalyst of about 0.1:1 to about 10:1. However, based on effectiveness as well as economic considerations, it is preferred to employ the catalyst and co-catalyst in a total amount of about 0.1 to about 4.0 weight percent, based on the weight of alkylbenzene and in a molar ratio of catalyst:co-catalyst of about 0.25:1 to about 2:1. At lower catalyst-:co-catalyst ratios some benzylic chlorination may occur whereas at higher ratios a lessening of the para-directing effect of the catalyst system may result.

Under atmospheric pressure, the chlorination reaction of the present invention may be carried out over a wide range of temperatures, ranging for example from sub-zero temperatures (Celsius scale) to over 100° C.

It is preferred to utilize temperatures in the range of about 0° to about 75° C, and most preferably in the range of about 20° to about 70° C. Although it is preferred to carry out the process at atmospheric pressures, subatmospheric or superatmospheric pressures may be employed if desired.

The alkylbenzenes which may be chlorinated in accordance with the present invention include the various straight chain and branched chain alkylbenzenes as well as substituted alkylbenzenes. The preferred alkylbenzenes are those wherein the alkyl group is 1 to 4 carbon atoms, and most preferably toluene. It will be appreciated that, although the preparation of monochloro alkylbenzenes, having a relatively high proportion of parachloro alkylbenzene, is an important object of the present invention, the monochloro product may be further chlorinated, if desired, to produce higher chlorinated derivatives.

The process of this invention may be carried out by chlorination of the alkylbenzene in solution or in the absence of a solvent. Suitable solvents which may be employed, if desired, include for example various halogenated solvents such as carbon tetrachloride, or aromatic solvents such as monochlorobenzene. It is preferred, however, to carry out the chlorination directly, in the absence of a solvent.

The following specific examples are provided to further illustrate this invention and the manner in which it may be carried out. It will be understood, however, that the specific details given in the examples have been chosen for purpose of illustration and are not to be construed as a limitation on the invention. In the examples, unless otherwise indicated, all parts and percentages are by weight and all temperatures are in degrees Celsius.

EXAMPLE 1

A mixture of 92.1 parts of toluene, 1.0 parts of antimony trichloride, and 1.0 parts of thianthrene was charged to a reaction vessel and heated to about 50° C. The temperature was maintained at about 50°–55° C while 36 parts of chlorine gas was introduced into the reaction mixture over a period of about 3 hours.

The reaction product was analyzed by gas chromatographic methods and found to contain approximately 43.0% toluene; 28.1% orthochlorotoluene; and 28.7% parachlorotoluene. The ratio of ortho:para isomer was 0.98.

EXAMPLES 2–18

The following Examples (2–18) set forth the ratio of orthochlorotoluene to parachlorotoluene (ortho:para) obtained when toluene was chlorinated in a manner similar to that described in Example 1, at a temperature of about 50° C in the presence of a catalyst system consisting of a thianthrene co-catalyst and various Lewis acid catalysts. Thianthrene was employed in various amounts (shown as weight percent, based on the amount of toluene) and the ratio of catalyst:co-catalyst was varied as shown.

| Example | Weight Percent of Thianthrene | Catalyst | Molar Ratio of Catalyst: Co-Catalyst | Ortho:Para Obtained |
|---|---|---|---|---|
| 2 | 2.0 | AlCl$_3$ | 0.5 | 0.91 |
| 3 | 0.25 | AlCl$_3$ | 0.5 | 1.13 |
| 4 | 0.25 | AlCl$_3$ | 1.0 | 0.96 |
| 5 | 0.1 | AlCl$_3$ | 1.0 | 1.11 |
| 6 | 0.5 | AlCl$_3$ | 1.5 | 1.18 |
| 7 | 0.25 | FeCl$_3$ | 0.25 | 1.40 |
| 8 | 2.0 | FeCl$_3$ | 0.5 | 1.04 |
| 9 | 1.0 | SbCl$_3$ | 1.0 | 1.03 |
| 10 | 0.1 | SbCl$_3$ | 0.25 | 1.23 |
| 11 | 0.5 | SbCl$_3$ | 1.0 | 1.10 |
| 12 | 1.0 | SbF$_3$ | 1.0 | 1.12 |
| 13 | 0.5 | SbF$_3$ | 1.0 | 1.15 |
| 14 | 1.0 | SbF$_5$ | 1.0 | 1.19 |
| 15 | 0.5 | SbF$_5$ | 1.0 | 1.43 |
| 16 | 2.0 | W(CO)$_6$ | 0.5 | 1.20 |
| 17 | 2.0 | MoCl$_5$ | 0.5 | 1.26 |
| 18 | 2.0 | ZrCl$_4$ | 0.5 | 1.50 |

What is claimed is:

1. A process for the preparation of nuclear chlorinated alkylbenzenes which comprises reacting an alkylbenzene with chlorine at a temperature of about 0° to about 100° Celsius and in the presence of a catalyst system comprising a Lewis acid catalyst and a thianthrene co-catalyst characterized by the formula

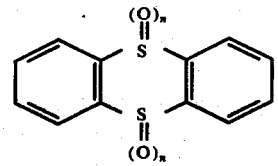

where each $n$ is 0 to 1.

2. A process according to claim 1 wherein the co-catalyst is thianthrene.

3. A process according to claim 2 wherein the alkyl group of said alkylbenzene is a branched or straight chain alkyl group of 1 to 4 carbon atoms.

4. A process according to claim 3 wherein the alkylbenzene is toluene.

5. A process according to claim 4 wherein the catalyst is a chloride of aluminum, antimony or iron.

6. A process according to claim 2 wherein the catalyst and co-catalyst are present in total amount of about 0.01 to about 5.0 weight percent based on the weight of alkylbenzene and the process is carried out at a temperature of about 0° to about 100° Celsius.

7. A process according to claim 6 wherein the molar ratio of catalyst:co-catalyst is about 0.1:1 to about 10:1.

8. A process according to claim 7 wherein the alkylbenzene is toluene.

9. A process according to claim 8 wherein the catalyst is antimony trichloride.

10. A process according to claim 8 wherein the catalyst is ferric chloride.

11. A process according to claim 8 wherein the catalyst is aluminum chloride.

12. A process for the preparation of monochlorotoluene which comprises reacting toluene with chlorine at a temperature of about 20° to about 70° C Celsius in the presence of about 0.1 to about 4.0 weight percent, based on the weight of toluene, of a catalyst system comprising a catalyst selected from the group consisting of chlorides of aluminum, antimony and iron, and a thianthrene co-catalyst, said catalyst and co-catalyst, being present in a molar ratio of catalyst:co-catalyst of about 0.25:1 to about 2:1.

* * * * *